(12) United States Patent
Mahoney et al.

(10) Patent No.: US 7,922,985 B2
(45) Date of Patent: Apr. 12, 2011

(54) ANALYTE TEST STRIP FOR ACCEPTING DIVERSE SAMPLE VOLUMES

(75) Inventors: John Mahoney, San Carlos, CA (US); Caroline Chu, Milpitas, CA (US); Herb Perasso, San Jose, CA (US); Susan Tannenbaum, Fremont, CA (US); Janice Jones, Pleasanton, CA (US); Koon-Wah Leong, Sunnyvale, CA (US); John Christopher Davis, Los Altos, CA (US)

(73) Assignee: Lifescan, Inc., Milpitas, CA (US)

( * ) Notice: Subject to any disclaimer, the term of this patent is extended or adjusted under 35 U.S.C. 154(b) by 389 days.

(21) Appl. No.: 12/145,314

(22) Filed: Jun. 24, 2008

(65) Prior Publication Data

US 2009/0317297 A1    Dec. 24, 2009

(51) Int. Cl.
*G01N 21/75* (2006.01)
(52) U.S. Cl. .................................................. 422/400
(58) Field of Classification Search ............ 422/56, 422/400
See application file for complete search history.

(56) References Cited

U.S. PATENT DOCUMENTS

| | | | |
|---|---|---|---|
| 5,120,420 A * | 6/1992 | Nankai et al. ............ 204/403.11 |
| 5,437,999 A | 8/1995 | Diebold et al. | |
| 5,563,042 A | 10/1996 | Phillips et al. | |
| 6,461,496 B1 | 10/2002 | Feldman et al. | |
| 6,885,196 B2 | 4/2005 | Taniike et al. | |
| 7,008,799 B1 | 3/2006 | Zimmer et al. | |
| 7,232,510 B2 | 6/2007 | Miyazaki et al. | |
| 2002/0100685 A1 | 8/2002 | Huang et al. | |
| 2005/0214171 A1 | 9/2005 | Gerstle et al. | |
| 2006/0076249 A1 | 4/2006 | Meisegeier et al. | |
| 2008/0118397 A1 | 5/2008 | Slowey et al. | |

FOREIGN PATENT DOCUMENTS

| | | |
|---|---|---|
| EP | 0287883 A1 | 10/1988 |
| EP | 1471354 A2 | 10/2004 |
| EP | 1571442 A1 | 9/2005 |
| EP | 1347302 B1 | 2/2007 |
| EP | 1770396 A2 | 4/2007 |
| WO | WO 9930152 A1 * | 6/1999 |
| WO | WO 01/75438 A2 | 10/2001 |
| WO | WO 2005/117556 A2 | 12/2005 |
| WO | WO 2006/107262 A1 | 10/2006 |

* cited by examiner

*Primary Examiner* — Bobby Ramdhanie

(57) ABSTRACT

An analyte test strip for accepting diverse bodily fluid sample volumes includes a first insulating layer, a second insulating layer disposed above the first insulating layer, and a third insulating layer disposed below the first insulating layer. The third insulating layer has a platform portion that extends beyond the first and second insulating layers and an upper surface. The analyte test strip also has a patterned spacer layer positioned between the first and second layers. The patterned spacer layer defines a channel between the first and second insulating layers that has a sample-receiving chamber, a first port proximate the platform portion and a second port at an outer edge of the analyte test strip. Moreover, the first port and the second port are in fluidic communication with the sample-receiving chamber. In addition, the upper surface of the platform portion is configured to receive a first (relatively large) bodily fluid sample of at least 5 micro-liters and transfer at least a portion of the first bodily fluid sample to the sample-receiving chamber via the first port. The second port is configured to receive a second (relatively small) bodily fluid sample of lesser volume than the first bodily fluid sample and to transfer at least a portion of the second bodily fluid sample to the sample-receiving chamber.

16 Claims, 5 Drawing Sheets

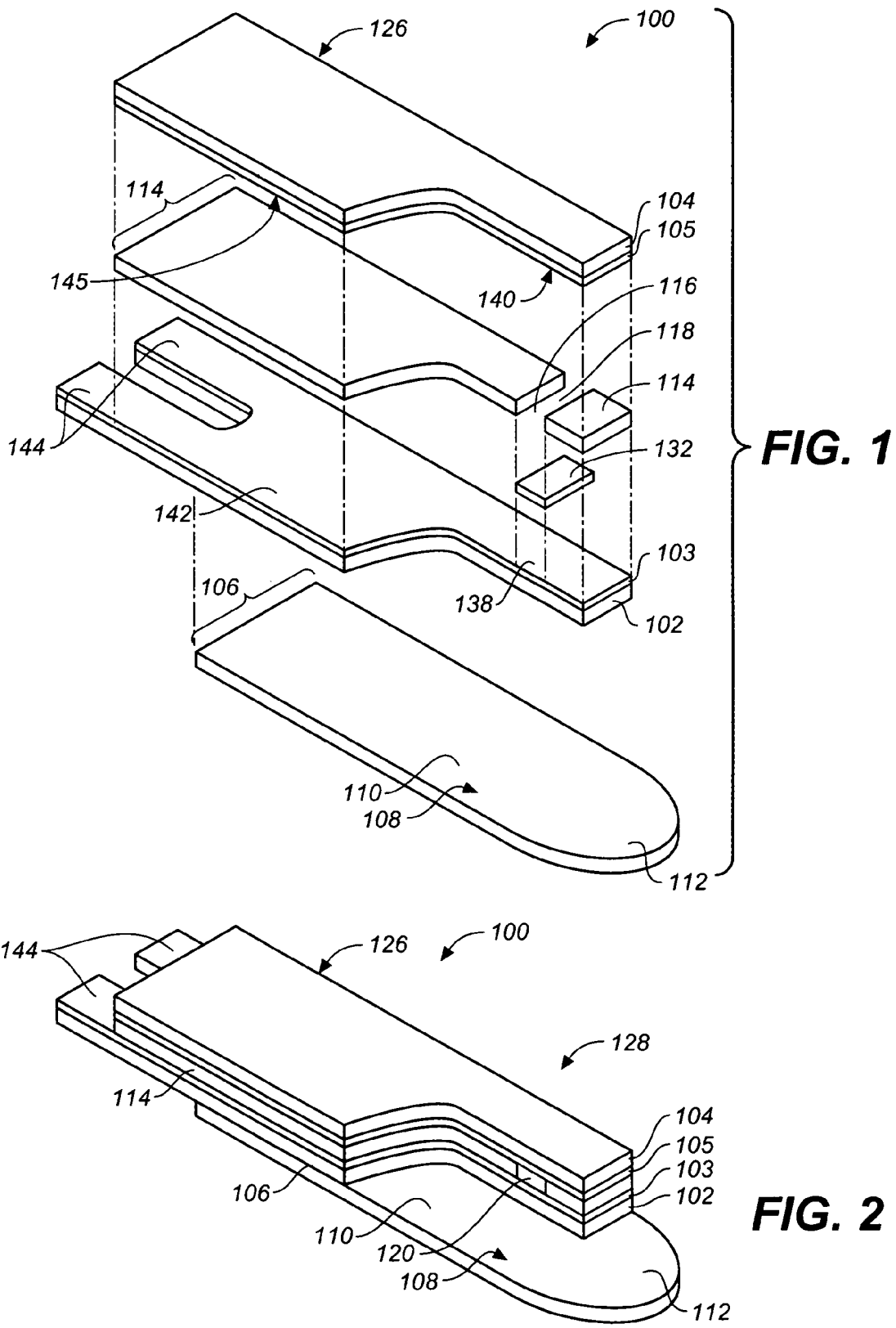

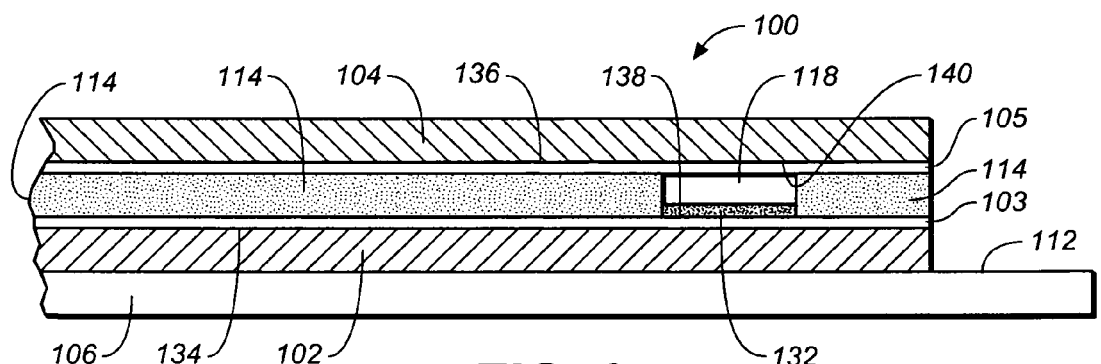
FIG. 3
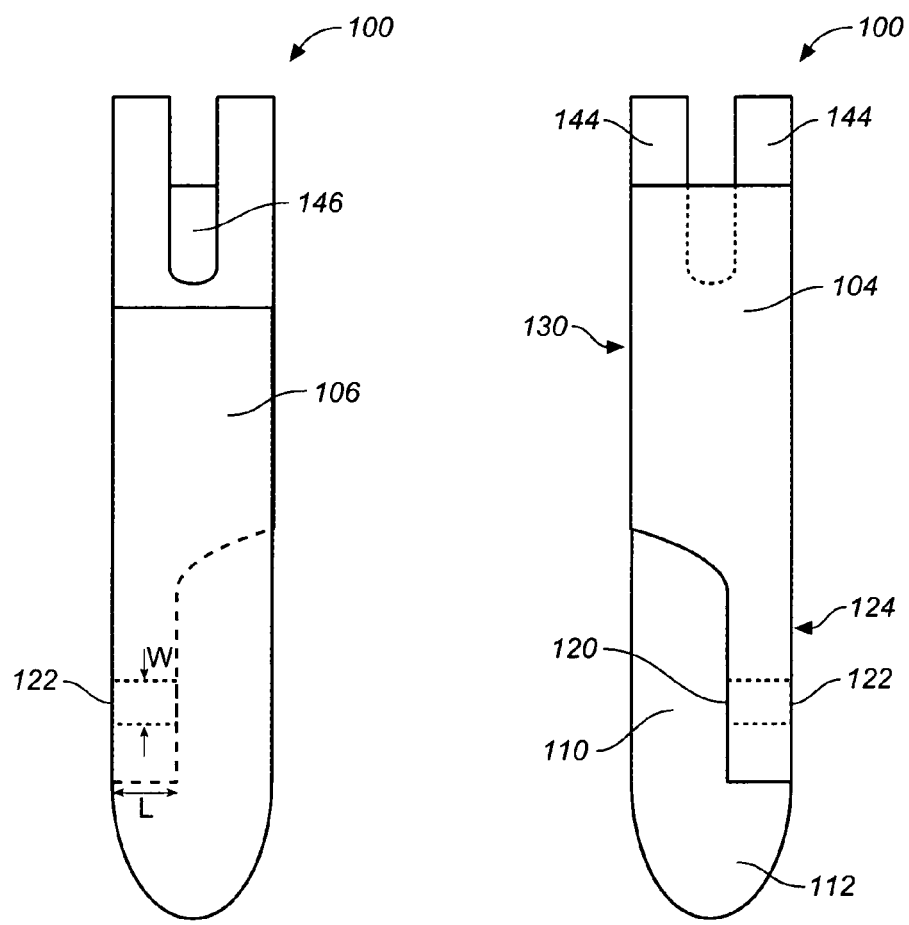
FIG. 4   FIG. 5

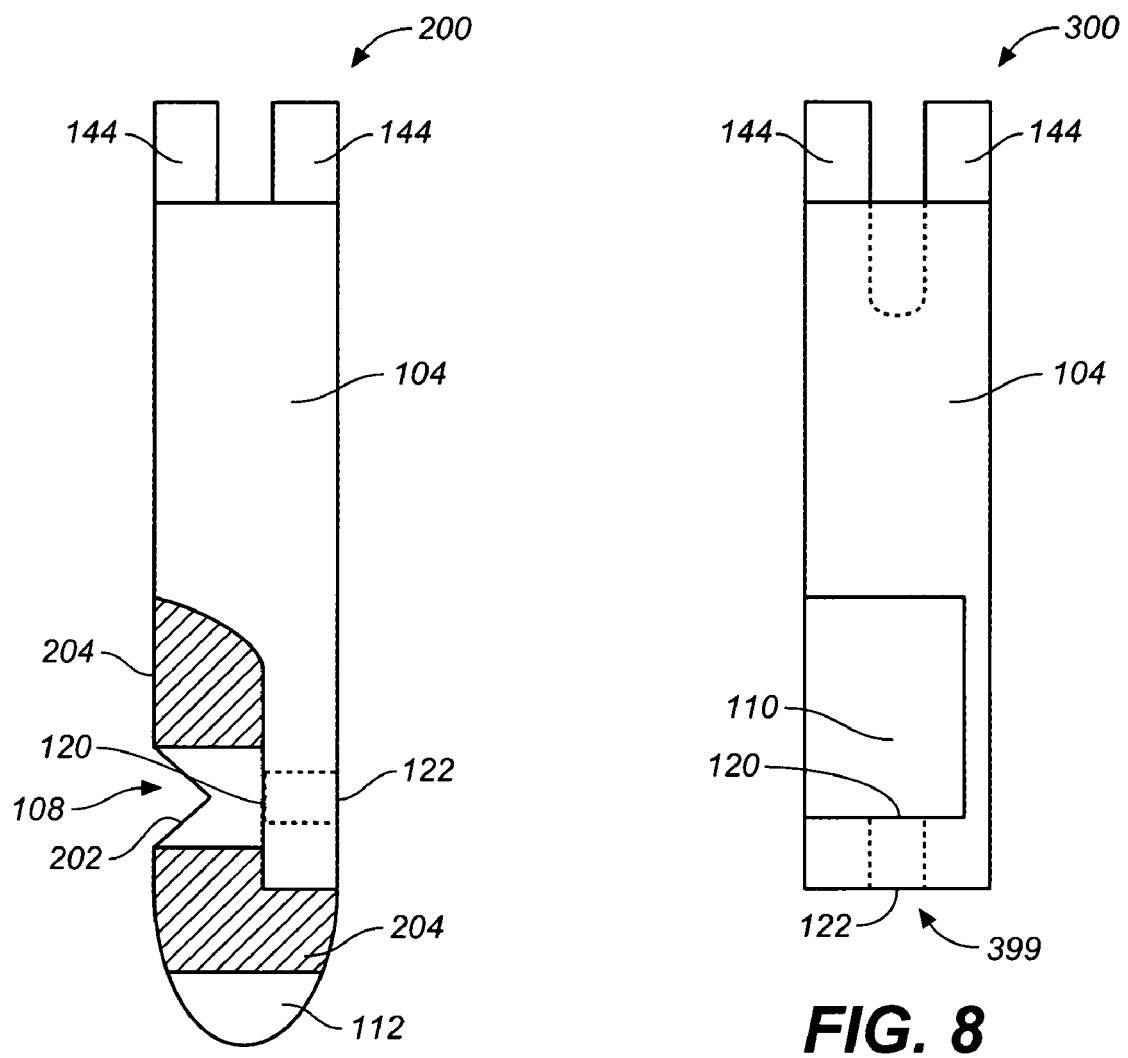

ANALYTE TEST STRIP FOR ACCEPTING DIVERSE SAMPLE VOLUMES

BACKGROUND OF THE INVENTION

Analyte determination, for example analyte detection and/or concentration measurement, in bodily fluid samples (e.g., a whole blood sample) is of increasing importance in today's society. Assays for analyte determination find use in a variety of settings, including clinical laboratories and homes. The results of such assays (also referred to as "tests") play a prominent role in the diagnosis and management of a variety of medical conditions. Analytes of medical interest include, for example, glucose and cholesterol. In response to the importance of analyte determination, a variety of analyte detection protocols and devices for both clinical and home use have become commercially available.

One type of analyte detection device is an analyte test strip that employs an electrochemical-based method to detect and/or measure the concentration of an analyte, such as glucose, in a bodily fluid sample (e.g., a whole blood sample). During such an electrochemical-based method, a bodily fluid sample is placed into a sample-receiving chamber of an analytical test strip that includes two electrodes, e.g., a counter electrode and a working electrode. The analyte is allowed to react with a redox reagent within the sample-receiving chamber to form an oxidizable (or reducible) substance in an amount corresponding to the analyte's concentration. The quantity of the oxidizable (or reducible) substance present is then measured electrochemically and related to the amount of analyte present in the initial bodily fluid sample. Such conventional analyte test strips are described in, for example, U.S. Pat. Nos. 5,708,247; 5,951,836; 6,241,862; and 6,284,125; each of which is hereby incorporated in full.

BRIEF DESCRIPTION OF THE DRAWINGS

The accompanying drawings, which are incorporated herein and constitute part of this specification, illustrate presently preferred embodiments of the invention, and, together with the descriptions herein, serve to explain features of the invention, in which:

FIG. 1 is a simplified, exploded, perspective view of an analyte test strip according to an embodiment of the present invention, wherein broken lines indicate alignment of various components;

FIG. 2 is a simplified perspective view of the analyte test strip of FIG. 1;

FIG. 3 is a simplified cross-section view of a portion of the analyte test strip of FIG. 1;

FIG. 4 is a simplified bottom plan view of the analytes test strip of FIG. 1 with dashed lines depicting selected features hidden from view in the perspective of FIG. 4;

FIG. 5 is a simplified top plan view of the analyte test strip of FIG. 1 with dashed lines depicting selected features hidden from view in the perspective of FIG. 5;

FIG. 6 is a simplified top plan view of an analyte test strip according to another embodiment of the present invention;

FIG. 8 is simplified top plan view of the analyte test strip of FIG. 7A with dashed lines depicting selected features hidden from view in the top plan view of FIG. 8;

DETAILED DESCRIPTION OF ILLUSTRATIVE EMBODIMENTS OF THE INVENTION

Figure 7A:
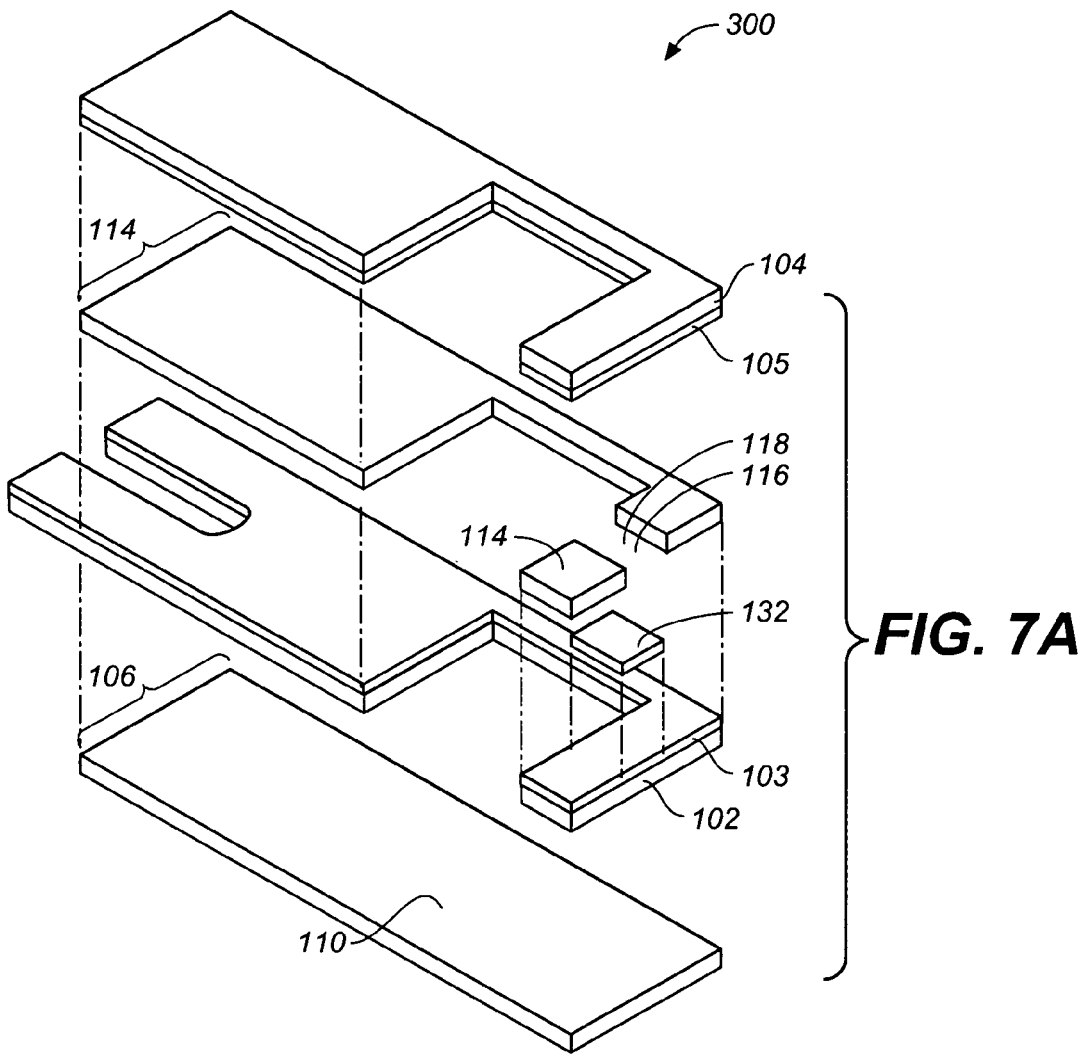
FIGS. 7A and 7B are a simplified, exploded, perspective view and a simplified perspective view respectively, of an analyte test strip according to yet another embodiment of the present invention, wherein the broken lines of FIG. 7A indicate alignment of various components.

The following detailed description should be read with reference to the drawings, in which like numbers indicate like elements. The drawings, which are not necessarily to scale, depict selected exemplary embodiments for the purpose of explanation only and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part, or collection of components, or method to function for its intended purpose as described herein. In addition, as used herein, the terms "patient", "host" and "subject" refer to any human or animal subject and are not intended to limit the systems or methods to human use, although use of the subject invention in a human patient represents a preferred embodiment.

Analyte test strip for accepting diverse bodily fluid sample volumes and determining an analyte according to embodiments of the present invention possess a variety of benefits. For example, the analyte test strips can be employed both in an institutional setting (e.g., a hospital or clinic) where bodily fluid sample volumes are large (e.g., greater than 5 microliters, and typically greater than 25 microliters) and in home settings where bodily fluid samples are small (for example, less than 5 microliters and frequently less than 1 microliter). Moreover, embodiments of the present invention also provide visual guidance for the application of large bodily fluid samples and/or a configuration that contains excess bodily fluid sample. Such containment of excess bodily fluid sample is beneficial in terms of avoiding bodily fluid contamination of associated equipment (e.g., a meter) and personnel.

Embodiments of the present invention are suitable for use in the determination of a wide variety of analytes in a broad variety of bodily fluid samples, and are particularly suited for use in the determination of analytes in whole blood, plasma, serum, interstitial fluid, or derivatives thereof, where an analyte of particular interest is glucose.

Referring to FIGS. 1 through 5, an analyte test strip 100 for accepting diverse bodily fluid sample volumes and determining an analyte therein includes a first insulating layer 102 (with first conductive layer 103 disposed thereon), a second insulating layer 104 (with second conductive layer 105 disposed thereon) disposed above first insulating layer 102 and a third insulating layer 106 disposed at least partially below first insulating layer 102.

Third insulating layer 106 includes a platform portion 108 that extends beyond first insulating layer 102 and second insulating layer 104. Platform portion 108 has an upper surface 110 configured to receive a bodily fluid sample of at least 5 microliters in volume and, preferably, greater than 25 microliters in volume. Such relatively large volumes are typically employed in institutional settings. Third insulating layer 106 also has a handle portion 112 that extends beyond first insulating layer 102 and second insulating layer 104 and is disposed proximally of platform portion 108.

Analyte test strip 100 also includes a patterned spacer layer 114 sandwiched between first insulating layer 102 and the second insulating layer 104. Patterned spacer layer 114 serves to define a channel 116 between first insulating layer 102 and second insulating layer 104. Moreover, as depicted clearly in FIGS. 1 and 2, a sample-receiving chamber 118 of analyte test strip 100 is formed by two interior edges of patterned spacer layer 114 and a capillary space between first conductive layer 103 (with regular layer 132 thereon) and second conductive layer 105. In addition, channel 116 has a first port 120 proximate to platform portion 108 and a second port 122 at a first outer lateral edge 124 of analyte test strip 100. It should be noted that first port 120 and second port 122 are in fluidic communication with sample-receiving chamber 118. In addition to first outer lateral edge 124, analyte test strip 100 also has a distal end 126, a proximal end 128, and a second lateral edge 130.

Once apprised of the present disclosure, one skilled in the art will recognize that in the embodiment of FIGS. 1 through 3, sample-receiving chamber 118 and channel 116 are essentially the same feature. However, one of skill in the art will also recognize that sample-receiving chamber 118 can also be a sub-portion of channel 116 depending on the shape and disposition of first and second conductive layers 103 and 105, respectively.

Upper surface 110 of platform portion 108 is configured to receive a first bodily fluid sample of at least 5 micro-liters (not shown in the FIGS.) and transfer at least a portion of that first bodily fluid sample to sample-receiving chamber 118 via first port 120. In addition, second port 122 is configured to receive a second bodily fluid sample (also not shown in the FIGS.) of lesser volume than the first bodily fluid sample and for transferring at least a portion of the second bodily fluid sample to sample-receiving chamber 118. Analyte test strip 100 also includes a reagent layer 132, as depicted in FIG. 1.

Once apprised of the present disclosure, one skilled in the art will recognize that the configuration of analyte test strip 100 beneficially provides for analyte determination in either of a first bodily fluid sample of relatively large volume (i.e., greater than 5 microliters and preferably greater than 25 microliters) or a second bodily fluid sample of smaller volume (such as less than 5 microliters or preferably less than 1 microliter). Hence, analyte test strips according to embodiments of the present invention can beneficially accommodate disparate bodily fluid sample volumes and be used in both institutional settings for large bodily fluid sample volumes and home settings for relatively small bodily fluid sample volumes.

In the embodiment of FIGS. 1-5, first conductive layer 103 is coated on inner surface 134 of first insulating layer 102. Second conductive layer 105 is coated on inner surface 136 of second insulating layer 104. The first and second conductive layers (103 and 105) serve to form a first electrode 138 and a second electrode 140 (see FIG. 3), respectively, bordering sample-receiving chamber 118. First conductive layer 103 also forms first connection track 142 and first contact pads 144, while second conductive layer 105 forms second connection track 145 and second contact pad 146.

First insulating layer 102 and second insulating layer 104 can be formed, for example, of a plastic (e.g., PET, PETG, polyimide, polycarbonate, polystyrene), silicon, ceramic, or glass material. For example, the first and second insulating layers can be formed from a 7 mil polyester substrate.

In the embodiment of FIGS. 1-5, first electrode 138, along with second electrode 140, are configured to electrochemically determine analyte concentration in a bodily fluid sample (such as glucose in a whole blood sample) using any suitable electrochemical-based technique known to one skilled in the art. First connection track 142 is a portion of first conductive layer 103 that electrically connects first electrode 138 to first contact pads 144. First contact pads 144 are configured to operatively connect to an associated meter. Second contact pad 146 is also configured to operatively connect to the associated meter.

Although FIG. 1 depicts only one electrode formed in each of the first and second conductive layers (103 and 105), one skilled in the art would recognize that more than one electrode could be formed from such conductive layers using, for example, an etching or patterned deposition technique. In an alternative embodiment, the first and second electrodes can be configured in a co-planar arrangement.

If desired, first conductive layer 103 and/or second conductive layer 105 can be coated with a solution containing 2-mercaptoethane sulfonic acid (MESA) and then dried. One purpose of such a MESA coating is to make the first and/or second conductive layer (103 and/or 105) hydrophilic and also to protect the first and/or second conductive layers (103 and/or 105) from being fouled by inadvertent organic compounds in the ambient air. Such a hydrophilic surface can also be beneficial in causing a bodily fluid sample to fill the sample-receiving chamber.

The first and second conductive layers, 103 and 105 respectively, can be formed of any suitable conductive material such as, for example, gold, palladium, carbon, silver, platinum, tin oxide, iridium, indium, or combinations thereof (e.g., indium doped tin oxide). Moreover, any suitable technique can be employed to form the first and second conductive layers including, for example, sputtering, evaporation, electro-less plating, screen-printing, contact printing, or gravure printing. For example, first conductive layer 103 can be a sputtered palladium layer and second conductive layer 105 can be a sputtered gold layer. The thickness of the first and second conductive layers can be, for example, about 10 nanometers or greater, and preferably range from about 10 nanometers to about 80 nanometers.

Patterned spacer layer 114 serves to bind together first insulating layer 102 (with first conductive layer 103 thereon) and second insulating layer 104 (with second conductive layer 105 thereon), as illustrated in FIGS. 1-5. Patterned spacer layer 114 can be, for example, a double-sided pressure sensitive adhesive layer, a heat activated adhesive layer, or a thermosetting adhesive plastic layer. In an embodiment, patterned spacer layer 114 is a double-sided cyano-acrylic pressure sensitive adhesive coated on opposing sides of a polyester sheet. In another embodiment, patterned spacer layer 114 is a thermoplastic sheet such as, for example Vitel, which is a linear saturated co-polyester resin having a relatively high molecular weight. The thermoplastic may be laminated at 70° C. to bind the two layers together.

Patterned spacer layer 114 can have, for example, a thickness in the range of from about 1 micron to about 500 microns, preferably between about 10 microns and about 400 microns, and more preferably between about 40 microns and about 200 microns. Note, that the thickness of patterned spacer layer 114 defines a capillary-dimensioned distance between first electrode 138 and second electrode 140 (see FIG. 3 in particular).

Channel 116 can have, for example, an area of ranging from about 0.01 $cm^2$ to about 0.2 $cm^2$, preferably about 0.02 $cm^2$ to about 0.15 $cm^2$, and more preferably about 0.03 $cm^2$ to about 0.08 cm². In an exemplary embodiment, channel 116 can have a width W of about 1.2 millimeters and a length L of about 3.5 millimeters, as illustrated in FIG. 4.

Reagent layer 132 can be any suitable mixture of reagents that selectively react with an analyte such as, for example glucose, in a bodily fluid sample to form an electroactive species, which can then be quantitatively measured at an electrode of analyte test strips according to embodiments of the present invention. Therefore, reagent layer 132 can include at least a mediator and an enzyme. Examples of suitable mediators include ferricyanide, ferrocene, ferrocene derivatives, osmium bipyridyl complexes, and quinone derivatives. Examples of suitable enzymes include glucose oxidase, glucose dehydrogenase (GDH) using a pyrroloquinoline quinone (PQQ) co-factor, GDH using a nicotinamide adenine dinucleotide (NAD) co-factor, and GDH using a flavin adenine dinucleotide (FAD) co-factor.

Reagent layer 132 can be manufactured by, for example, dispensing a suitable reagent formulation onto a first electrode and/or second electrode of analyte test strip 100. After dispensing the reagent formulation, a drying process can be used to remove water from the reagent formulation, thereby forming reagent layer 132. An exemplary embodiment of a reagent formulation can include 33 mM potassium citraconate, pH 6.8, 0.033% Pluronic P103, 0.017% Pluronic F87, 0.85 mM $CaCl_2$, 30 mM sucrose, 286 μM PQQ, 15 mg/mL GDH, and 0.6 M ferricyanide. Pluronics are a block copolymers based on ethylene oxide and propylene oxide, which can function as antifoaming agents and/or wetting agents. An exemplary embodiment for printing a reagent formulation is a dispensing process from the end of a 13 gauge needle poised about 150 μm above a conductive layer.

In one embodiment, reagent layer 132 may have an area larger than the area of first electrode 138. As a result, a portion of patterned spacer layer 114 can overlap and be in contact with reagent layer 132. Therefore, patterned spacer layer 114 can be configured to form a liquid impermeable seal to first electrode 138 even though a portion of reagent layer 132 is between patterned spacer layer 114 and first electrode 138. For example, patterned spacer layer 114 may intermingle with or partially dissolve a portion of reagent layer 132 to thereby form a liquid impermeable bond to first electrode 138 sufficient to define an operational electrode area.

Based on the area of channel 116 and the patterned spacer layer 114 thickness that was previously described above, the volume of the sample-receiving chamber 118 can range from about 0.1 microliters to 5 microliters, preferably about 0.2 microliters to about 3 microliters, and more preferably about 0.3 microliters to about 1 microliter.

Platform portion 108 and handle portion 112 provides a beneficial increase in handleability. Handleability refers to the ability of a user to generally manipulate an analyte test strip, which includes removing a test strip from a container, inserting the test strip into an associated meter, and removing a used analyte test strip from the test meter without the user being contaminated with bodily fluid.

Platform portion 108 can have, for example, an area that is greater than or equal to about 4 mm², and preferably greater than or equal to about 56 mm². Platform portion 108 may extend outwardly from first port 120 for a distance of greater than or equal to about 2 mm, and preferably greater than or equal to about 7 mm.

In one embodiment of an analyte test strip according to the present invention, an upper surface of a platform portion is configured to be less hydrophilic than a sample-receiving chamber of the analyte test strip such that capillary forces will cause filling of the sample-receiving chamber via a channel.

Once the sample-receiving chamber is filled with a portion of a first bodily fluid sample, an excess amount of the first bodily fluid sample may remain on the platform portion.

A relatively large volume of bodily fluid is generally available when a bodily fluid sample is collected (e.g., withdrawn) at a hospital, clinic or other institutional setting. For example, blood can be withdrawn using a syringe through a venous puncture, or obtained through a venous or arterial catheter. In this situation, blood may be deposited on an analytical test strip by expressing a relatively large drop of blood at an end of hypodermic needle, a syringe or a pipette. It should be noted that when using a syringe or pipette, it is difficult to express a relatively small drop of blood, where a small volume may be, for example, about twenty microliters or less, and preferably about five microliters or less. Typical syringes or pipettes in a hospital setting are not designed to dispense such a small volume. Further, typical syringes or pipettes do not easily create a hanging drop that can be guided to a port on an edge of an analytical test strip. Thus, when using a syringe, pipette tip or other device that can only generate relatively large bodily fluid drops, an analyte test strip that can be dosed from above onto a platform portion (such as analyte test strip 100) makes the dosing process easier and decreases the likelihood of spilling bodily fluid onto a counter-top, floor or user. Moreover, in some circumstances a user may desire to apply a control solution to an analytical test strip. Conventional control solutions are stored in containers with dispensing tips that result in relatively large drops of control solution. Such relatively large drops of control solution can be difficult to apply to a port on an edge of an analytical test strip but can be easily applied to the platform portion of analytical test strips according to embodiments of the present invention.

In contrast to the hospital setting, bodily fluid samples of relatively small volume are generally available in a home setting. For example, blood can be withdrawn using a lancing device that pricks a user's fingertip or alternative target site (e.g., forearm, palm or thigh). A relatively small droplet of blood can then be expressed from the user's skin layer. When using a fingertip, a user can create a hanging drop and move the fingertip to apply the hanging drop as a second (small) bodily fluid sample to an analyte test strip. When using an alternative site such as a forearm, a user typically moves the test strip inserted in or other wise attached to an associated meter to the expressed blood sample. Applicants have discovered that small volumes of bodily fluid are easily applied to a port located on an edge of an analytical test strip (such as the second port illustrated in FIGS. 4 and 5). In such an embodiment, blood expressed from a finger can be placed contiguous to the second port to fill a sample-receiving chamber. In such a use, the second port acts as an inlet port for the liquid to ingress and the first port can act as a vent/outlet port for air to egress.

Because a user may need to test, or be tested, in either an institutional setting (e.g., a hospital) or home setting, analytical test strips according to embodiments of the present invention are beneficially versatile due to a configuration that provides for the use of disparate (diverse) bodily fluid sample volumes.

Referring to FIG. 6, an analyte test strip 200 for accepting diverse bodily fluid sample volumes and determining an analyte therein is depicted. Analyte test strip 200 is identical to analyte test strip 100 of FIGS. 1-5 except for the addition of two additional features (i.e., a notch and two bodily fluid absorbent pads) that are described below. Therefore, many elements of analyte test strip 200 are numbered using like numbering from FIGS. 1-5 and for simplicity will not be described further here.

Analyte test strip 200 includes a platform portion 108 with a notch 202 formed therein and two bodily fluid absorbent pads 204 disposed thereon (see FIG. 6). Bodily fluid absorbent pads 204 are configured to absorb and retain excess amounts of a first (large) bodily fluid (not shown) that has been received on platform portion 108 but not transferred to a sample-receiving chamber of analyte test strip 200. A beneficial function of the bodily fluid absorbent pads 204 is to reduce any likelihood of transferring bodily fluid to a user or other inadvertent location during use of analyte test strip 200. The purpose of notch 202 is the provision of general visual guidance to a user in regards to where the user is to dose a bodily fluid sample of relatively large volume on analyte test strip 200.

Figure 7B:
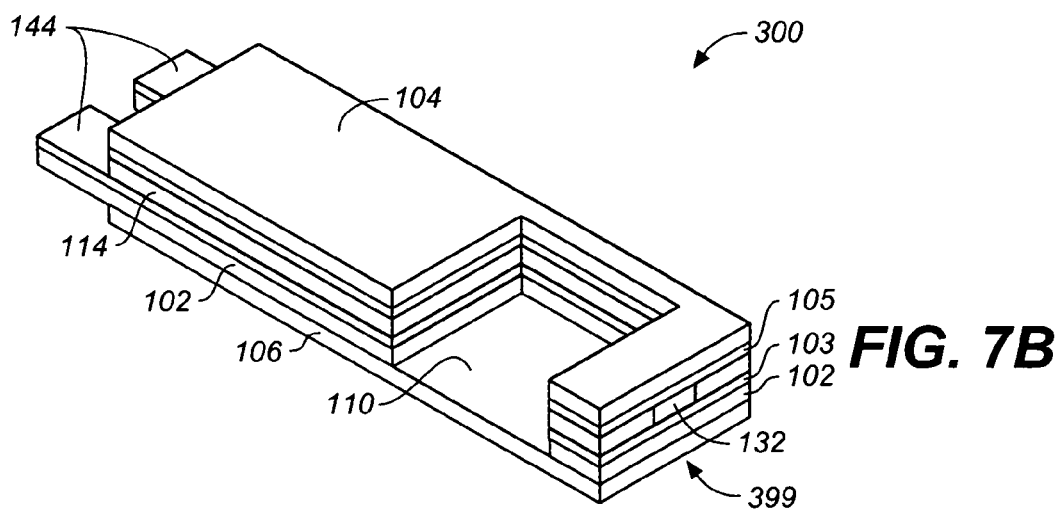

Referring to FIGS. 7A, 7B and 8, an analyte test strip 300 for accepting diverse bodily fluid sample volumes and determining an analyte therein according to another embodiment of the present invention is depicted. Analyte test strip 300 is essentially similar to analyte test strip 100 of FIGS. 1-5 except for (i) the absence of handle portion 112 and (ii) analyte test strip 300 is configured such that second port 122 is at an a proximal end outer edge of analyte test strip 300 (described further below). Therefore, elements of analyte test strip 300 are numbered using like numbers from FIGS. 1-5 and for simplicity such like elements are not be described further.

As noted above, second port 122 of analyte test strip 300 is positioned at a proximal end outer edge 399 of analyte test strip 300. Positioning second port 122 at a proximal end outer edge of the analyte test strip is beneficial with respect to providing a readily locatable port for users that are dosing the analyte test strip with a bodily fluid sample expressed from a target site such as the user's fingertip. In other words, it is hypothesized, without being bound, that some user's may find it easier to locate a second port positioned on a proximal end outer edge of the analytical test strip than to find a second port positioned on a lateral edge of the analytical test strip.

Although FIGS. 1-8 depict an analyte test strip configured for electrochemical-based analyte determination, once apprised of the present disclosure one skilled in the art will recognize that analyte test strips according to embodiments of the present invention can also be configured for analyte determination via colorimetric techniques or any other suitable analyte determination technique.

Figure 9:
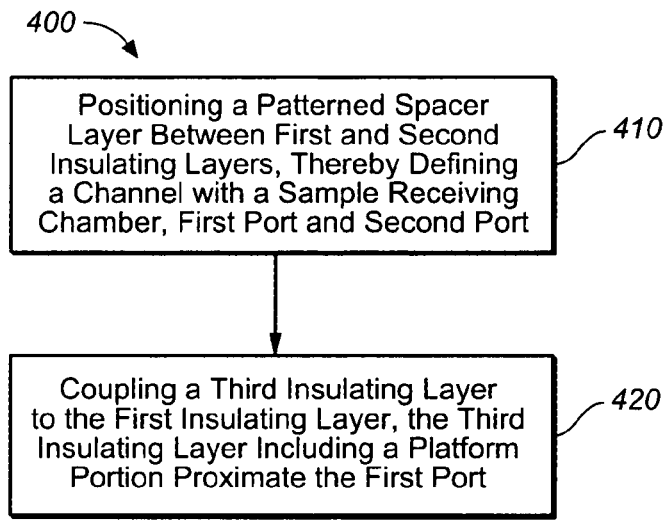
FIG. 9 is a flow diagram depicting stages of a method for manufacturing an analyte test strip according to an embodiment of the present invention.

FIG. 9 is a flow diagram depicting stages of a method 400 for manufacturing an analyte test strip according to an embodiment of the present invention including. Method 400 can be employed, for example, to manufacture the analyte test strips described above with respect to FIGS. 1-5, 6, 7A, 7B and 8.

Method 400 includes, at step 410, positioning a patterned spacer layer between a first insulating layer and a second insulating layer. Step 410 is accomplished such that the second insulating is disposed above the first insulating layer and the patterned spacer layer defines a channel between the first insulating layer and the second insulating layer. Moreover, the channel has a sample-receiving chamber therein, a first port and a second port.

Method 400 also includes coupling a third insulating layer to the first insulating layer such that the third insulating layer is disposed at least partially below the first insulating layer, as set forth in step 420.

In method 400, the third insulating layer includes a platform portion that extends beyond the first and second insulating layers and has an upper surface proximate to the first port. Moreover, (i) the first port and the second port are in fluidic communication with the sample-receiving chamber, (ii) the upper surface of the platform portion is configured to receive a first bodily fluid sample of at least 5 microliters and for filling the sample-receiving chamber with a portion of the first bodily fluid sample, and (iii) the second port is configured to receive a second bodily fluid sample of lesser volume than the first bodily fluid sample and for filling the sample-receiving chamber with a portion of the second bodily fluid sample.

Once apprised of the present disclosure, one skilled in the art will recognize that method 400 can be readily modified to include steps that result in the manufacturing of analyte test strips with any of the beneficial features and characteristics described herein with respect to analyte test strips of the present invention.

Figure 10:
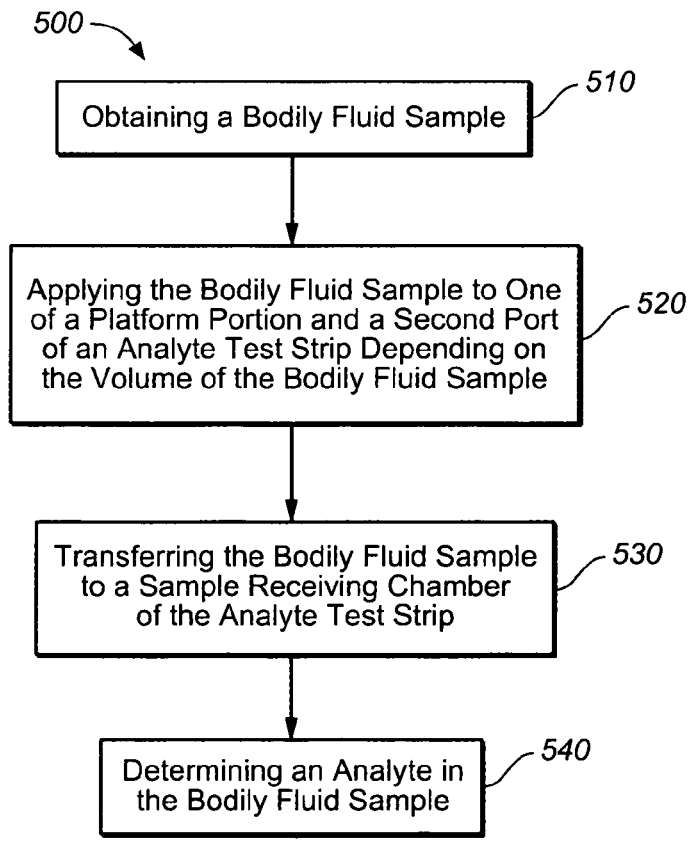
FIG. 10 is a flow diagram depicting stages of a method for determining an analyte in a bodily fluid sample according to an embodiment of the present invention.

FIG. 10 is a flow diagram depicting stages of a method 500 for determining an analyte (such as glucose) in a bodily fluid sample (for example, a whole blood sample) according to an embodiment of the present invention. In regard to method 500, the term "determining" refers to detection and/or concentration measurement.

Method 500 includes obtaining a bodily fluid sample such as, for example, a whole blood sample, as set forth in step 510. The bodily fluid sample can be obtained using any suitable technique known to one of skill in the art including, in particular, those described herein with respect to institutional and home settings.

Subsequently, the bodily fluid sample is applied to an analyte test strip (see step 520). Once apprised of the present disclosure, one skilled in the art will recognize that the bodily fluid sample can be applied, for example, to an analytical test strip according to embodiments of the present invention including those described above with respect to FIGS. 1-5, 6, 7A, 7B and 8. The applying step involves applying the bodily fluid sample to one of a second port and a platform portion of the analyte test strip depending on the volume of the bodily fluid sample.

At step 530, the applied bodily fluid sample is transferred to a sample-receiving chamber of the analyte test strip. Then, at step 540, an analyte in the bodily fluid sample is determined using, for example, an electrochemical based technique.

In general, the analyte test strip employed in method 500 includes a first port in fluidic communication with the sample-receiving chamber and proximate a platform portion of the analyte test strip. Moreover, the platform portion is configured to receive a first bodily fluid sample of at least 5 micro-liters and transfer at least a portion of the first bodily fluid sample to the sample-receiving chamber via the first port. The analyte test strip also includes the aforementioned second port in fluidic communication with the sample-receiving chamber and an outer edge of the analyte test strip, the second port configured to receive a second bodily fluid sample of lesser volume than the first bodily fluid sample and for transferring at least a portion of the second bodily fluid sample to sample-receiving chamber.

Once apprised of the present disclosure, one skilled in the art will recognize that the first bodily fluid sample can be considered a relatively "large" sample and the second bodily fluid sample a relatively "small" sample. Moreover, one skilled in the art will also recognize that a user will apply either a first (large) bodily fluid sample or a second (small) bodily fluid sample, but will not apply both a first and a second bodily fluid sample to the same analytical test strip.

Method 500 can be readily modified by one skilled in the art to incorporate any of the techniques, benefits and characteristics of analyte test strips according to embodiments of the present invention and described herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. Various alternatives to the embodiments of the invention described herein may be employed in practicing the invention. It is intended that the following claims define the scope of the invention and that methods and structures within the scope of these claims and their equivalents be covered thereby.

What is claimed is:

1. An analyte test strip for accepting diverse bodily fluid sample volumes and determining an analyte therein, the analyte test strip comprising:
 a first insulating layer;
 a second insulating layer disposed above the first insulating layer;
 a third insulating layer disposed at least partially below the first insulating layer, the third insulating layer including:
  a platform portion that extends beyond the first insulating layer and the second insulating layer, the platform portion having an upper surface;
 a patterned spacer layer positioned between the first insulating layer and the second insulating layer, the patterned spacer layer defining:
  a channel between the first insulating layer and the second insulating layer, the channel having:
   a sample-receiving chamber therein:
   a first port proximate the platform portion and
   a second port at an outer edge of the analyte test strip;
 wherein the first port and the second port are in fluidic communication with the sample-receiving chamber; and
 wherein the upper surface of the platform portion extends outwardly from the first port and is configured to receive a first bodily fluid sample of at least 5 micro-liters and transfer at least a portion of the first bodily fluid sample to the sample-receiving chamber via the first port; and
 wherein the second port is configured to receive a second bodily fluid sample of lesser volume than the first bodily fluid sample and for transferring at least a portion of the second bodily fluid sample to sample-receiving chamber.

2. The analyte test strip of claim 1 wherein the third insulating layer also has a handle portion extending beyond the first insulating layer and second insulating layer and disposed proximally of the platform portion.

3. The analyte test strip of claim 1 wherein the upper surface of the platform portion is configured to retain an excess portion the first bodily fluid sample.

4. The analyte test strip of claim 1 further comprising:
 a first electrode; and
 a second electrode,
  wherein the first electrode and second electrode are disposed on the first insulating layer; and
  wherein the first electrode and second electrode are configured for electrochemical-based determination of an analyte in either of the first bodily fluid sample second bodily fluid sample.

5. The analyte test strip of claim 1 further comprising:
 a first electrode disposed on the first insulating layer; and
 a second electrode disposed on the second insulating layer.

6. The analyte test strip of claim 1 wherein the second bodily fluid sample is a blood sample expressed from a finger positioned proximate to the second port.

7. The analyte test strip of claim 1, wherein the first bodily fluid sample is a blood sample received on the upper surface of the platform from one of a syringe and a pipette.

8. The analyte test strip of claim 1 wherein the platform portion has a surface free energy predetermined to cause at least a portion of the first bodily fluid sample to enter the channel via the first port.

9. The analyte test strip of claim 1 further comprising:
 an absorbent layer disposed on the platform portion, the absorbent layer being configured to absorb an excess volume of the first bodily fluid sample.

10. The analyte test strip of claim 1 wherein the platform portion has a notch configured to guide an application of the first bodily fluid sample to the upper surface of the platform portion.

11. The analyte test strip of claim 1, in which the platform portion has an area in the range of from about 4 $mm^2$ to about 56 $mm^2$.

12. The analyte test strip of claim 1 wherein the first bodily fluid sample has a volume of at least 25 micro-liters and the second bodily fluid sample has a volume of less than 1 micro-liter.

13. The analyte test strip of claim 1 wherein the second port is at an outer lateral edge of the analyte test strip.

14. The analyte test strip of claim 1 wherein the second port is at an outer proximal end edge of the analyte test strip.

15. The analyte test strip of claim 1 wherein the analyte test strip is configured for electrochemical-based determination of an analyte.

16. The analyte test strip of claim 1 wherein the analyte test strip is configured for colorimetric-based determination of an analyte.

* * * * *